United States Patent
Brockmann et al.

(10) Patent No.: US 11,925,317 B2
(45) Date of Patent: Mar. 12, 2024

(54) METHOD FOR PRODUCING A SURGICAL HANDHELD DEVICE, AND A SURGICAL HANDHELD DEVICE

(71) Applicant: OLYMPUS WINTER & IBE GMBH, Hamburg (DE)

(72) Inventors: Christian Brockmann, Hollenstedt (DE); Andreas Offt, Reinbek (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 265 days.

(21) Appl. No.: 17/375,163

(22) Filed: Jul. 14, 2021

(65) Prior Publication Data
US 2022/0015607 A1    Jan. 20, 2022

(30) Foreign Application Priority Data

Jul. 14, 2020   (DE) .................. 10 2020 118 536.7

(51) Int. Cl.
| | |
|---|---|
| *A61B 1/00* | (2006.01) |
| *A61B 1/31* | (2006.01) |
| *B21D 26/045* | (2011.01) |
| *B21D 26/049* | (2011.01) |
| *B21D 39/04* | (2006.01) |

(Continued)

(52) U.S. Cl.
CPC ........ *A61B 1/0011* (2013.01); *A61B 1/00066* (2013.01); *A61B 1/00137* (2013.01); *A61B 1/31* (2013.01); *B21D 26/045* (2013.01); *B21D 26/049* (2013.01); *B21D 39/04* (2013.01); *B21D 26/041* (2013.01); *B21D 26/047* (2013.01); *Y10T 29/49805* (2015.01)

(58) Field of Classification Search
CPC ............. Y10T 29/498; Y10T 29/49911; B21D 26/041; B21D 26/045; B21D 26/049; A61B 1/0011; A61B 1/00066
See application file for complete search history.

(56) References Cited

U.S. PATENT DOCUMENTS

| | | | |
|---|---|---|---|
| 2010/0038893 A1 | 2/2010 | Stolle et al. | |
| 2012/0047979 A1* | 3/2012 | Hertell | B21D 26/045 72/58 |

(Continued)

FOREIGN PATENT DOCUMENTS

| | | |
|---|---|---|
| DE | 8717221 U1 | 9/1988 |
| DE | 19957508 C1 | 1/2001 |

(Continued)

*Primary Examiner* — Jermie E Cozart
(74) *Attorney, Agent, or Firm* — Oliff PLC

(57) ABSTRACT

A surgical handheld devices are essentially made up of a device body or main body and of a tubular shaft. In the production of known surgical devices, the tubular shafts are welded to the device bodies. A large number of very complex work steps are necessary for this purpose. On account of the high quality demands placed on surgical handheld devices in respect of mechanical stability and sterility, the weld seam has to meet the most stringent requirements. The invention makes available a method for producing a surgical handheld device, which can be used particularly easily and reliably. This is achieved by the fact that at least one device body and at least one tubular shaft of a surgical handheld device are connected to each other with form-fit engagement by hydroforming.

6 Claims, 2 Drawing Sheets

(51) Int. Cl.
*B21D 26/041* (2011.01)
*B21D 26/047* (2011.01)

(56) References Cited

U.S. PATENT DOCUMENTS

2014/0239038 A1* 8/2014 Leimbach ........ A61B 17/07207
227/175.1
2020/0205814 A1 7/2020 Shelton, IV et al.

FOREIGN PATENT DOCUMENTS

| | | |
|---|---|---|
| DE | 102005045008 A1 | 3/2007 |
| DE | 102008038276 A1 | 2/2010 |
| DE | 102016118158 B3 | 1/2018 |
| JP | 2001-095814 A | 4/2001 |
| JP | 2016-508421 A | 3/2016 |
| WO | 2014/133861 A1 | 9/2014 |

* cited by examiner

METHOD FOR PRODUCING A SURGICAL HANDHELD DEVICE, AND A SURGICAL HANDHELD DEVICE

The invention relates to a method for producing a surgical handheld device that can include a device body and a tubular shaft that are connected by hydroforming.

Surgical handheld devices, for example endoscopes, resectoscopes, cystoscopes and the like, are essentially made up of a device body or main body and of a tubular shaft. In the production of known surgical devices, the tubular shafts are welded to the device bodies. To do this, a large number of in some cases highly complex and time-consuming work steps are necessary. For example, the tubular shaft first of all has to be expanded on a mandrel, and the expanded end of the shaft then has to be pressed into the device body or into a cone of the device body. Finally, the two structural parts of the surgical handheld device are welded to each other. On account of the high quality demands placed on surgical handheld devices in respect of mechanical stability and sterility, the weld seam has to meet the most stringent requirements. These requirements can be achieved only with great effort, and, in the final analysis, it can never be ascertained whether the weld seam still meets the requirements even after repeated use of the device.

The problem addressed by the present invention is to make available a method for producing a surgical handheld device, and a surgical handheld device, which permits particularly simple and reliable production.

A solution to this problem is described with respect to a method for producing a surgical handheld device as described further below. Accordingly, provision is made that at least one device body and at least one tubular shaft of a surgical handheld device, in particular of an endoscope, a resectoscope, a cystoscope or the like, are connected with form-fit engagement to each other by hydroforming. By this hydroforming method, the at least one shaft can be connected with form-fit engagement to the at least one device body in a very simple and reliable manner. By virtue of the simplicity and the high degree of reproducibility of this connection, it is possible not only to produce a high-quality device but also to reduce the production costs.

In particular, provision is made according to the invention that the at least one device body is a main body, an attachment body or a cone of the device body. Equally, however, it is also conceivable that other bodies of surgical devices, for example an optical plate, can be connected according to the invention to the at least one tubular shaft.

Moreover, provision is preferably made according to the invention that the at least one tubular shaft is a shaft, a tube or an outer or inner tube. In addition, it is conceivable that further shaft-like or tubular components of a surgical handheld device can be connected with form-fit engagement to the aforementioned body in the manner according to the invention. By virtue of the method described here, all connections between bodies and tubular shafts can thus be made in a simple and reliable manner.

The method according to the invention also includes connections between several bodies and several shafts. For example, a continuous tubular shaft can be designed with a variable cross section as a shaft tube (distally in the insertion region) and an optics guide tube (proximally between main body and optical plate). The main body can then be placed centrally onto this shaft, and the optical plate can be placed at the end thereof. By means of the hydroforming method, both bodies can then be fixed simultaneously or successively on the shaft or connected to the shaft. It is equally conceivable that two shafts in one body, or two bodies with two shafts, etc., can be connected to each other. Equally, it is also conceivable that several shafts are connected to each other with form-fit engagement by the method according to the invention.

In the method according to the invention, provision is preferably made that a portion, preferably an end portion or a middle portion, of the at least one tubular shaft is first of all guided into an opening or into a receiving space of the at least one device body. Depending on the nature and shape and design of the device or of the device body, the shaft is guided by a suitable distance into this space. The portion in question can be a straight portion, but also in particular a curved portion of the shaft. Thereafter, the at least one device body and the at least one tubular shaft are fixed at least regionally in at least one mold, which is preferably composed of two mold halves. This orientation and fixing of the components in the mold or the mold parts can be effected manually or by machine or semiautomatically or fully automatically. In addition, it is also conceivable that the mold is composed of several mold parts. The mold or the mold parts are precisely designed such that they form a complement or a negative of the shapes of the device body and of the shaft. By virtue of this fixing of the components in the mold, it is ensured during the method that both the shape of the device body and also the region of the shaft outside the device body do not deform. However, it is also conceivable that the mold parts have at least regionally a different shape than the stated components, such that the shape of the components can be changed locally. In the next step, open ends of the at least one device body and/or of the at least one tubular shaft are closed by sealing means. These sealing means can be valves, screw closures or pressure closures or other kinds of stoppers. By way of at least one valve, which is preferably integrated in one of the sealing means, a pressure, in particular a hydraulic or a pneumatic pressure, is then built up. By means of this pressure, the at least one region of the at least one tubular shaft, which is located inside the receiving space of the device body, is adapted to an inner contour of the device body. This widening of the portion results in the form-fit connection between the tubular shaft and the device body. This connection produced by the hydroforming method satisfies the most stringent quality demands placed on surgical handheld devices. By subsequent reduction of the pressure and opening of the mold, the connection between the tubular shaft and the body is at least almost ready.

In a further preferred illustrative embodiment of the invention, provision is made that the inner contour of the at least one device body has at least one ring-like undercut and/or at least one projection against which the at least one tubular shaft is pressed with form-fit engagement. This undercut or projection or the recess gives additional strength to the connection between the shaft and the body. In particular, forces acting axially on the shaft can thus be taken up, specifically without the connection between the components being destroyed. It is moreover conceivable that the inner contour has a multiplicity of undercuts and/or projections.

Preferably, provision can also be made that the at least one tubular shaft is subjected to a predefined pressure, or the pressure is increased until a sufficiently firm form-fit connection is produced. The pressure acting on the inner wall of the shaft can be regulated both via the valve and at an external generator, which is connected to the shaft via a corresponding feed line. The pressure to which the shaft is subjected can be regulated depending on the material of the components and on the shape and dimension of the shaft. In order to build up a sufficiently high pressure for the form-fit connection, preselected pressure values can be adjusted, or the change in the pressure can be used as an indicator of the expansion of the shaft.

A surgical handheld device for solving the problem mentioned at the outset is described below. Accordingly, provision is made that the surgical handheld device, which is an endoscope, a resectoscope, a cystoscope or the like, can be produced. The surgical handheld device is essentially made up of at least one device body, or a main body, an attachment body or a cone of the device body, and of an optical plate or another component. Moreover, the handheld device is composed of at least one tubular shaft, a tube or an outer tube or an inner tube. The at least one body has a receiving space, or a cone which is slightly larger in cross section than the cross section of the tubular shaft. Otherwise, the cross section of the shaft corresponds to the inner contour of the receiving space.

Both the device body and the shaft can be made of a metal, for example stainless steel, titanium or the like. These materials can be shaped particularly effectively by the hydroforming method.

Furthermore, provision can be made according to the invention that an inner contour of the at least one device body has at least one ring-like undercut and/or at least one projection against which the at least one tubular shaft is pressed with form-fit engagement. The form fit between the stated components can be improved by means of these undercuts or projections.

Besides the surgical devices mentioned here, it is conceivable that other devices can also be produced by the described measures and/or can have the features mentioned.

A preferred illustrative embodiment of the invention is described in more detail below with reference to the drawing, in which.

Figure 1:
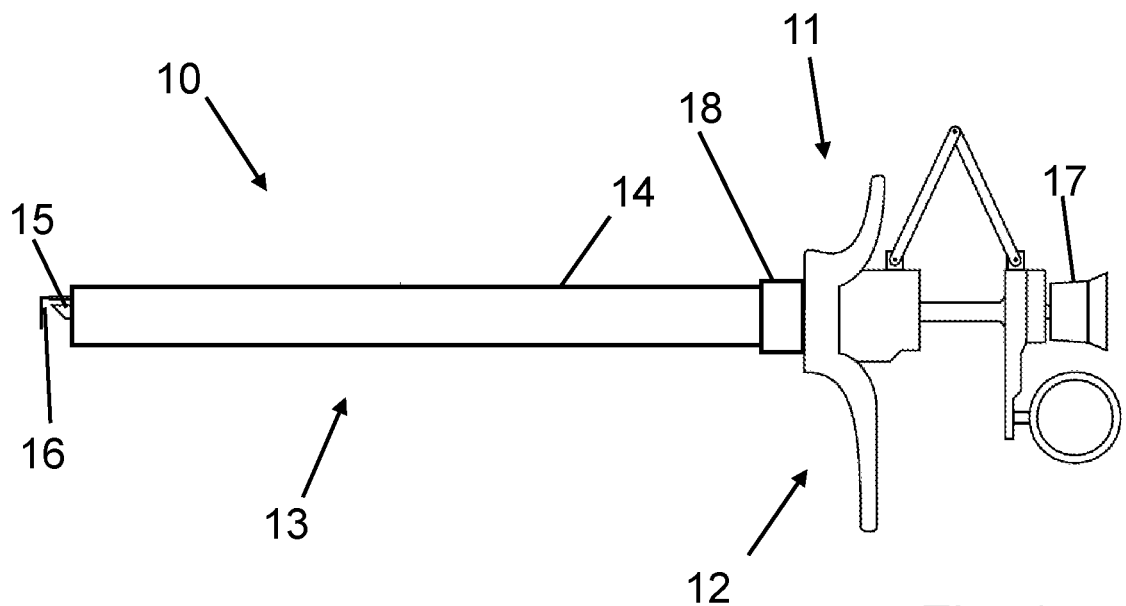
FIG. 1 shows a schematic view of a resectoscope.

FIG. 1 shows a resectoscope 10 as an example of a surgical handheld device. This resectoscope 10 is essentially made up of a transporter 11, a grip unit 12 and a shaft 13. It is expressly noted that the surgical handheld device can also be a device other than the resectoscope 10 shown here. The resectoscope 10 shown in FIG. 1 serves only to illustrate the invention. As has already been stated, the measures and features according to the invention can also be transposed to other surgical devices and can also be implemented simultaneously or successively on a plurality of components or bodies and shafts.

In the illustrative embodiment of a surgical handheld device shown here, the shaft 13 is composed of an outer shaft tube 14, an optical unit 15 and an electrode instrument 16. The optical unit 15 is composed of a long tube in which lenses or glass fibers can be arranged, such that a region at the distal end of the shaft 13 can be observed through an eyepiece 17 arranged proximally on the shaft 13. For a more detailed description of the resectoscope 10 shown here, reference is made to the known prior art.

As is customary, the surgical handheld device or resectoscope 10 shown in FIG. 1 also has a device body 18. This device body 18, also referred to as main body or attachment body, is an essential part of the device. For example, the grip unit 12 can be arranged on each main body 18, or further components for manipulation or control of the instrument. In the case of the resectoscope 10 shown here, the optical unit 15 inter alia is guided through the device body 18.

Figure 2:
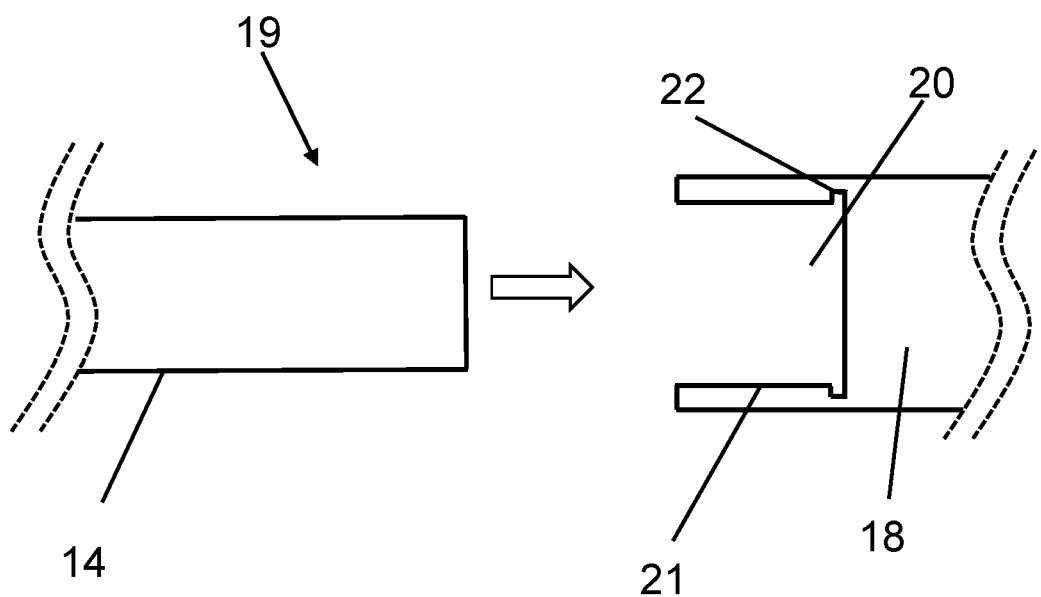
FIG. 2 shows a schematic partial view of a main body and of a shaft.
Figure 3:
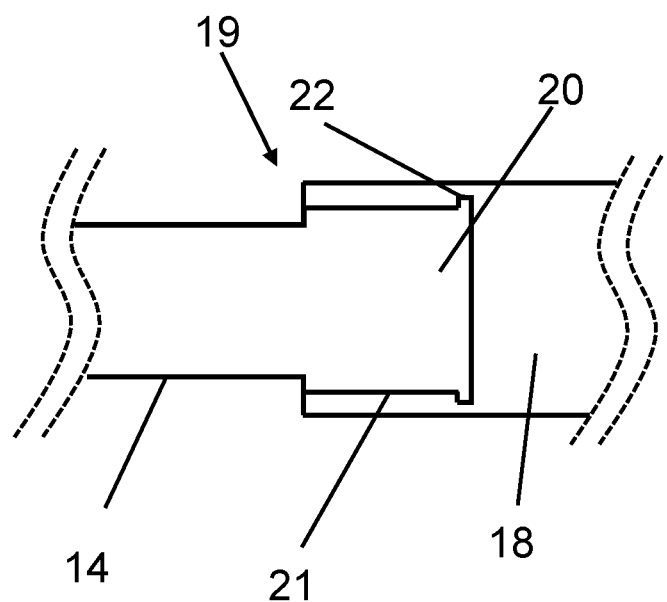
FIG. 3 shows a schematic partial view of a main body and of a shaft.

The tubular shaft 13 is firmly connected to the device body 18. Depending on the nature of the surgical handheld device, different instruments are guided in the shaft 13, as a result of which they are protected against external influences. According to the present invention, a proximal end region 19 of the shaft 13 is connected with form-fit engagement in a receiving space 20 of the housing body 18. To do this, the end region 19 of the shaft 13 is first of all guided into the receiving space 20 of the body 18 (FIG. 2). When the shaft 13 is subjected to a hydraulic pressure, the distal end region of the shaft 13 adapts to an inner contour 21 of the device body 18 (FIG. 3). The inner contour 21 of the device body 18 can have a ring-like undercut 22 in which the shaft 13 fits. By this expansion of the proximal end region 19 of the shaft 13, the form-fit connection is produced. This is shown highly schematically in FIG. 3.

In the method described here for producing the surgical handheld device, an external diameter of the shaft 13 is only negligibly smaller than the internal dimensions of the receiving space 20 of the device body 18. If the difference between these dimensions were too great, the reshaping of the shaft 13 or the adaptation of the circumference of the shaft 13 to the inner contour 21 would lead to an unsatisfactory result. On the one hand, a form-fit connection could not be produced, or at best only an inadequate form-fit connection could be produced, and, on the other hand, the shape of the shaft 13, or of the end region 19 of the shaft 13, would probably change in such a way as to cause a material weakness. If the difference between said dimensions is only slight, the outer circumference of the shaft 13 adapts optimally to the inner contour 21 of the device body 18, specifically without the shape or the material nature of the shaft 13 being adversely affected by the reshaping process. Moreover, by virtue of this relatively slight reshaping, less force needs to be applied.

To ensure that the force acting on the wall of the shaft 13 reshapes only the end region 19 of the shaft 13, and not the entire shaft and the main body, provision is made according to the invention that, prior to the application of pressure, both the device body 18 and the shaft 13, which is already positioned in the receiving space 20, are enclosed by a mold (not shown here). This mold can ideally consist of two halves. However, it is also conceivable that the mold, in particular for complex shapes of the device body 18, can be composed of a plurality of elements. The mold, in particular the assembled mold, is designed in such a way that it withstands the pressure acting on the shaft 13 and thus prevents a reshaping of the shaft 13 and of the body 18.

However, it is also conceivable that the mold or the mold elements have undercuts or the like, such that the components, in particular the shaft 13, of the handheld device undergo additional reshaping when pressure is applied. By means of this additional reshaping, the components can be prepared for special uses or requirements.

The hydraulic or pneumatic pressure is applied by a corresponding generator (not shown). This generator is connected to the shaft 13 and/or to the device body 18 via a line and a connector. For regulated or controlled generation of pressure, at least one valve can be arranged between the line and the stated components. The coupling of the line or of the valve to the shaft 13 or to the device body 18 can be effected via a special connector or flange or the like. After completion of the reshaping process, the pressure is reduced and the connection is uncoupled. Thereafter, the components simply have to be cleaned with the fluid that may be used.

The reshaping of the shaft portion or the form-fit connection between the shaft 13 and the device body 18 is thus reduced to a small number of steps that are easy to perform.

With the insertion of the shaft end 19 into the receiving space 20, the fixing of the components in the mold and the application of pressure, the method is particularly simple and reproducible. At least some of these steps can be performed fully automatically, such that this method according to the invention also reduces costs.

In this method, the cross section of the shaft 13 is not limited to a circle or ring. Instead, the cross section of the shaft 13 and the cross section of the receiving space 20 can also have another shape, for example an ellipse or possibly an oval or the like. Polygonal cross-sectional shapes are also conceivable. Through a combination of several in particular differently shaped undercuts 22 and preferably projections on the inner contour 21 of the device body 18, it is possible to produce a particularly reliable and stable form-fit connection.

Besides the embodiments shown in FIGS. 2 and 3, in particular as regards the shape of the receiving space 20, of the inner contour and of the undercuts 22, shapes other than those shown here are also provided.

The invention claimed is:

1. A method for producing a surgical handheld device, having at least one tubular shaft and at least one device body, wherein:
   connecting at least one device body and at least one tubular shaft with form-fit engagement by hydroforming;
   guiding at least one portion, of the at least one tubular shaft into a receiving space of the at least one device body;
   fixing the at least one device body to the at least one tubular shaft together;
   sealing open ends of the at least one device body and/or of the at least one tubular shaft;
   building up a hydraulic pressure in the at least one shaft;
   pressing the at least one portion of the at least one tubular shaft, which is located inside the receiving space of the at least one device body, by pressure applied to an inner contour of the at least one device body, as a result of which the form-fit connection between the at least one tubular shaft and the at least one device body is generated.

2. The method as claimed in claim 1 for producing a surgical handheld device, wherein the at least one device body is a main body or an attachment body or a cone of the device body or a further component of the handheld device.

3. The method as claimed in claim 1 for producing a surgical handheld device, wherein the at least one tubular shaft is a shaft, a tube or an outer tube or an inner tube.

4. The method as claimed in claim 1 for producing a surgical handheld device, wherein an inner contour of the at least one device body has at least one undercut and/or at least one projection against which the at least one tubular shaft is pressed with form-fit engagement.

5. The method as claimed in claim 1 for producing a surgical handheld device, wherein the at least one tubular shaft is subjected to a predefined pressure, or the pressure is increased until a sufficiently firm form-fit connection is produced.

6. The method as claimed in claim 1 for producing a surgical handheld device, wherein the at least one device body is an optical plate.

\* \* \* \* \*